United States Patent [19]

Gerson et al.

[11] Patent Number: 5,409,820
[45] Date of Patent: Apr. 25, 1995

[54] **PROCESS FOR THE PRODUCTION OF LOVASTATIN USING *CONIOTHYRIUM FUCKELII***

[75] Inventors: Donald F. Gerson; Xinfa Xiao, both of Winnipeg, Canada

[73] Assignee: Apotex, Inc., Ontario, Canada

[21] Appl. No.: 102,787

[22] Filed: Aug. 6, 1993

[51] Int. Cl.$^6$ .................. C12P 17/06; A01N 43/32; C07D 313/04
[52] U.S. Cl. .................. 435/125; 435/135; 435/254.1; 514/452; 549/271; 549/292
[58] Field of Search .................. 435/135, 254.1, 243, 435/125; 514/452; 549/271, 292

[56] References Cited

U.S. PATENT DOCUMENTS

| | | | |
|---|---|---|---|
| 3,983,140 | 10/1976 | Endo et al. | 260/343.5 |
| 4,049,495 | 10/1977 | Endo et al. | 195/36 |
| 4,137,322 | 1/1979 | Endo et al. | 424/273 |
| 4,231,938 | 11/1980 | Monaghan et al. | 260/343.5 |
| 4,246,258 | 1/1981 | Ayers et al. | 424/93 |
| 4,710,313 | 12/1987 | Miyajima et al. | 252/105 |

FOREIGN PATENT DOCUMENTS

| | | | |
|---|---|---|---|
| 1046439 | 1/1979 | Canada | 195/129 |
| 1129794 | 8/1982 | Canada | 195/86 |
| 1161380 | 1/1984 | Canada | 195/129 |

OTHER PUBLICATIONS

Akira Endo, J. Antibiotics, 32(8):852–854; "Monacollin K, a New Hypocholesterolemic Agent Produced by a Monascus Species"; Aug. 1979.
Akira Endo, Masao Kuroda and Yoshio Tsujita; J. Antibiotics, 29(12): 1346–1348; ML–236A, ML–236B, and ML–236C, "New Inhibitors of Cholesterogenesis Produced by *Penicillium citrinum*"; Dec. 1976.
A. Endo, Y. Tsujita, M. Kuroda and K. Tanzawa; Eur. J. Biochem., 77:31–36; "Inhibition of Cholesterol Synthesis in Vitro and in Vivo by ML–236A and ML–236B. Competitive Inhibitors of 3-Hydroxy-3Methylglutaryl–Coenzyme a Reductase"; Feb. 1977.
Allan G. Brown and Terry C. Smale; J.C.S. Perkin I, 1(11):1165–1170; "Crystal and Molecular Structure of Compactin, a New Antifungal Metabolite from *Penicillium brevicompactum*"; 1976.
A. W. Alberts et al.; Proc. Natl. Acad. Sci., 77(7):3957–3961, "Mevinolin: a Highly Potent Competitive Inhibitor of Hydroxymethylglutaryl–Coenzyme a Reductase and a Cholesterol–Lowering Agent"; Jul. 1980.
Akira Endo, Masao Kuroda and Kazuhiko Tanazawa; FEBS Letters, 72(2):323–326, "Competitive Inhibition of 3–Hydroxy-3-Methylglutaryl Coenzyme a Reductase by ML–236A and ML–236B Bungal Metabolites, Having Hypocholesterolemic Activity"; Dec. 1976.
ATCC Catalogue of Fungi/Yeasts, 17th Ed., 1987, p. 115.

*Primary Examiner*—Douglas W. Robinson
*Assistant Examiner*—Maria Luisa Osoteo
*Attorney, Agent, or Firm*—Nixon & Vanderhye

[57] ABSTRACT

A novel microorganism, *Coniothyrium fuckelii* ATCC 74227, and a process of using the microorganism for the production of lovastatin comprising fermenting *Coniothyrium fuckelii* ATCC 74227 or a lovastatin-producing mutant thereof in a nutrient medium containing assimilable sources of carbon, nitrogen, and inorganic salts under aerobic fermentation conditions.

10 Claims, No Drawings

PROCESS FOR THE PRODUCTION OF LOVASTATIN USING *CONIOTHYRIUM FUCKELII*

BACKGROUND OF THE INVENTION (i) Field of the Invention

The present invention relates to a process for preparing hypocholesteremic products, e.g., Lovastatin and Mevastatin.

(ii). Description of the Prior Art

High blood cholesterol levels are recognized as being one of the main causes of cardiopathy, e.g., cardiac infarction, arteriosclerosis or hyperlipaemia.

It is currently believed that a causative factor in such diseases is the deposition of cholesterol in the body, particularly within the arteries. As a result, considerable research has been undertaken with a view to discovering physiologically acceptable substances which are capable of inhibiting cholesterol biosynthesis and thus are capable of reducing blood cholesterol levels. Several patents have issued directed to such compounds and their process for production.

In one such patent, namely U.S. Pat. No. 3,983,140 patented Sep. 28, 1976 by A. Endo et al and its corresponding Canadian Patent 1,046,439 patented Jan. 16, 1979, a physiologically-active substances of the Formula 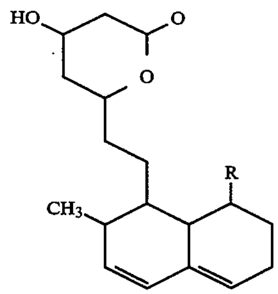 wherein R is hydrogen atom, hydroxy group or 2-methylbutyryloxy group, had been found to have cholesterol- and lipid-lowering effects in blood and liver and thus had utility as hypocholesteremic and hypolipemic medicaments. Such compounds were obtained by cultivation of a species of microorganisms belonging to the genus Penicillium, i.e., *Penicillium citrinum* in a culture medium and subsequent recovery thereof from a cultured broth.

In another such patent, namely U.S. Pat. No. 4,231,938, patented Nov. 4, 1980 by R. L. Monaghan et al, a compound having the lactone structure 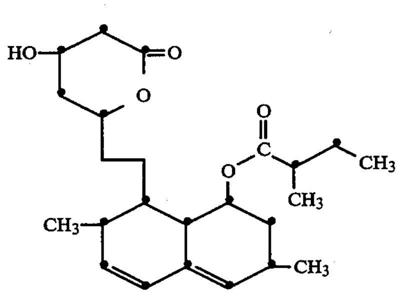 as well as its free hydroxy acid form had been found to form a class of highly active hypocholesteremic and hypolipemic medicaments. Such compounds were isolated after cultivation of a microorganism belonging to the genus Aspergillus in a culture medium.

In still another such patent, namely Canadian Patent 1,129,794 patented Aug. 17, 1982 by A. Endo, a compound having the formula 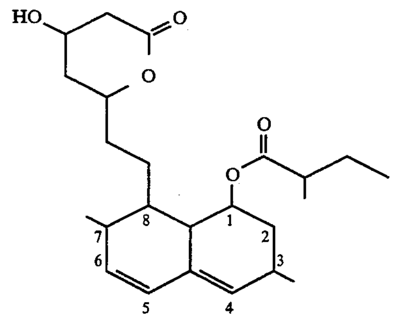 was found to be an antihypercholesteraemic agent. Such compound was prepared by cultivating a microorganism of the genus Monascus, e.g., *Monascus ruber*, particularly *Monascus ruber* strain 1005 (FERM 4822) in a suitable culture medium.

In yet another such patent, namely Canadian Patent 1,161,380 patented Jan. 31, 1984 by R. L. Monaghan et al, hypocholesteremic products were obtained from the cultivation of a microfungus of the species Aspergillus, e.g., *Aspergillus terreus.*

One commercially-available such compound is Lovastatin, having the formula

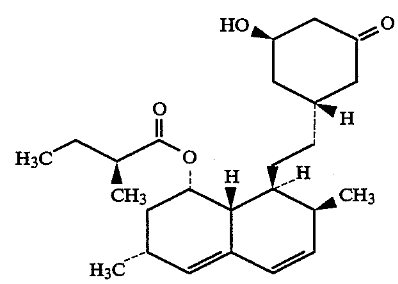

This compound has been found to be a potent inhibitor of HMB-CoA reductase, the rate controlling enzyme in cholesterol biosynthesis. Fermentation procedures for the preparation of this compound have been patented, namely in the above-identified Canadian Patent No. 1,046,439.

Another commercially-available such compound is Mevastatin having the formula this compound also has been found to be a potent inhibitor of HMG-CoA reductase, the rate controlling enzyme in cholesterol biosynthesis. One patented procedure for the preparation of such compound is the above-identified U.S. Pat. No. 3,983,140.

SUMMARY OF THE INVENTION

(i) Aims of the Invention

An object of this invention is to provide a novel fermentation technique for the production of cholesterol biosynthesis inhibiting (hypocholesteremic) substances.

Another object of this invention is the provision of a new strain of microorganism useful in the production of such substances.

(ii) Statement of Invention

The present invention provides a process for the production of hypocholesteremic compounds which comprise fermenting a microorganism of the genus Coniothyrium in a suitable medium, e.g., a medium containing glucose, corn starch, soybean flour, meat extract, peptone and sodium, potassium and magnesium salts, the medium having a slightly acidic pH, and recovering such compounds therefrom.

The present invention also provides a process for the preparation of Lovastatin which comprises fermenting Coniothyrium fuckelii ATCC 74227 in a suitable medium containing glucose, corn starch, soybean flour, meat extract, peptone and sodium, potassium and magnesium salts under the medium having a slightly acidic pH, and recovering Lovastatin therefrom.

The present invention also provides a process for the preparation of Mevastatin which comprises fermenting Coniothyrium fuckelii ATCC 74227 in a suitable medium, e.g., a medium containing glucose, corn starch, soybean flour, meat extract, peptone and sodium, potassium and magnesium salts under the medium having a slightly acidic pH, and recovering Mevastatin therefrom.

(iii) Other Facets of the Invention

By one important feature of this invention the fermentation medium comprises:
Glucose—3–15%
Corn Starch—0.5–1.5%
Soybean Flour—1–3%
Meat Extract—0.3%–0.7%
Amicase—0–5.0%
Peptone—0.5%–4%
$(NH_4)_2SO_4$—0.2–1.0%
NaCl—0.1%–0.3%
$KH_2PO_4$—0.03%–0.07%
$MgSO_4.7H_2O$—0.03%–0.2%
Antifoam agent—0.03%–0.07% (the polyglycol antifoam known by the trade-mark P2000$_{TM}$)
pH—5.0–6.0
L—isoleucine—0–1.5%
L—aspartic acid—0–1.5%

By another important feature of this invention the vegetative cells of the genus Coniothyrium are grown in a pre-culture medium to provide developed spores. Preferably, the pre-culture medium has the composition:
Glucose—2%±1%
Malt Extract—1%±0.5%
Neopeptone—2%±0.5%
pH—6.8±0.3

By another feature of this invention, the fermentation is carried out under submerged conditions.

By still another feature of this invention, the fermentation is carried out at a temperature of about 15° C. to about 37° C., preferably at a temperature of from about 22° C. to about 30° C.

By yet another feature of this invention, the pH of the nutrient medium is from about 4.0 to about 7.0.

By still another feature of this invention a novel organism is provided, namely Coniothyrium fuckelii, ATCC 14227.

(iv) Generalized Description of the Invention

The present invention is based on the observation that Lovastatin and Mevastatin are produced by the cultivation of a microorganism very different from that employed by Endo and Monaghan and as described above in relation to the referred-to patents. The microorganism is of the genus Coniothyrium. Based upon taxonomic studies, this Coniothyrium, was isolated and identified as a hitherto undescribed strain of microorganism. A strain thereof, referred to as Coniothyrium fuckelii, AFI-4 was deposited on Jun. 14, 1993, under accession ATCC 74227 with the American Type Culture Collection, 12301 Parklawn Drive, Rockville, Md. 20852. Other organisms of the genus Coniothyrium, including mutants of the above-described strain are believed to be capable of producing hypocholesteremic compounds, and in particular Lovastatin and Mevastatin.

It has surpisingly been found that a particular culture medium as described above produces commercial quantities of Lovastatin and Mevastatin. Thus, while it is theoretically possible to use the same aqueous media as those which have been previously employed for the production of other fermentation products, and which contain generic sources of carbon, nitrogen and inorganic salts assimilable by the microorganism, such use is discouraged according to the teachings of this invention.

While it is theoretically possible to use other carbohydrates, as have been previously employed for the production of other fermentation products, e.g., sugars, for example, fructose, maltose, sucrose, xylose, mannitol and the like, and other starches, e.g., example, oats, rye, corn meal, dextrose, dextrin, oat flour, oatmeal, molasses, citrate, soybean, oil, glycerol, malt extract, cod liver oil, starch, ethanol, figs, sodium ascorbate and lard oil and the like alone or in combination as sources of assimilable carbon in the nutrient medium, such use is discouraged according to the teachings of the present invention.

The exact quantity of the carbohydrate source or sources utilized in the medium depend in part upon the other ingredients of the medium but, in general, the amount of carbohydrate usually varies between about 3–15% by weight of the aqueous medium.

While it is theoretically possible to use other proteinaceous materials, as have been previously employed for the production of other fermentation products, as nitrogen sources in the fermentation process, e.g., yeast hydrolysates, primary yeast, cottonseed flour, hydrolysates of casein, corn steep liquor, distiller's solubles or tomato paste, peptonized milk, autolyzed yeast, yeast RNA, tomato paste, casein, primary yeast, peanut meal, distillers solubles, corn steep liquor, soybean meal, corn meal, NZ amine, beef extract, asparagine, cottonseed meal and ammonium sulfate, and the like, such use is discouraged according to the teachings of this invention. The sources of nitrogen either alone or in combination, are used in amounts ranging from about 3.0±1% by weight of the aqueous medium.

While it is theoretically possible to use the same nutrient inorganic salts as have been previously employed for the production of other fermentation products, e.g., salts capable of yielding sodium, potassium, ammonium calcium, phosphate, sulfate, chloride, carbonate, trace metals such as cobalt, manganese, iron and magnesium, e.g., $KH_2PO_4$, $MgSO_4.7H_2O$ and NaCl and small amounts of $COCl_2.6H_2O$ and traces of Fe, Nm, Mo, B and Cu, such use, other than the specific salts described above in the fermentation medium, is discouraged.

The fermentation may be carried out at any suitable temperature, i.e., temperatures ranging from about 15° C. to 37° C.; however, for optimum results it is preferable to conduct the fermentation at temperatures of from about 20° C. to 30° C.

The pH of the nutrient media suitable for growing the Coniothyrium culture and producing the novel compounds can vary from about 4.0 to 7.0.

Although the hypocholesteremic compounds are produced by both surface and submerged cultures, it is preferred to carry out the fermentation in the submerged state. A small scale fermentation is conveniently carried out by inoculating a suitable nutrient medium with the Coniothyrium culture and, after transfer to a production medium, permitting the fermentation to proceed at a convenient temperature of about 24° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 24° C. for 2 days, or until growth is satisfactory, and some of the resulting growth is used to inoculate either a second stage seed or the production medium.

For large scale commercialization, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 3 to 15 days while agitating and/or aerating the nutrient medium and maintaining the temperature at about 28° C.

At the end of the culture period, the hypocholesteremic compounds can be recovered from the culture by the use of per se conventional techniques which are suited to the physico chemical properties of such compounds. For example, the fermentation broth is acidified to approximately pH3, heated at approximately 75° C. for 4 hours and then filtered. The recovered solids are then extracted with a suitable solvent such as octane, toluene or methylenedichloride.

DESCRIPTION OF PREFERRED EMBODIMENTS

Example 1

Experiments were carried out using a pre-culture stage of 2 different durations to allow vegetative cells to develop from the spores of Coniothyrium sp. ATCC 74227 before the cultivation in shake flasks to produce Lovastatin.

The media were identified and composed as follows:

| ME | |
|---|---|
| Glucose | 2% |
| Malt Extract | 2 |
| Neopeptane | 0.3 |
| PH | 6.8 |
| 2MY | |
| Malt Extract | 4% |
| Yeast Extract | 1.6 |
| pH | 5.7 |
| Y5 | |
| Lactose | 6% |
| Ardamine PH | 1 |
| Soy protein | 0.2 |
| Betaine | 0.06 |
| KCl | 0.2 |
| $KH_2PO_4$ | 0.08 |
| $MnSO_4$ | 0.003 |
| P2000 | 0.1 |
| pH | 6.8 |

| CMP | DMP |
|---|---|
| Glucose - 3.5% | Glucose - 2% |
| Corn starch - 1% | Malt Extract - 0.2% |
| Soybean Flour - 2% | Peptone - 0.2% |
| Meat Extract - 0.5% | $KH_2PO_4$ - 0.2% |
| Peptose - 0.5% | $MgSO_4.7H_2O$ - 0.2% |
| NaCl - 0.2% | P2000 is a polyglycol |
| $KH_2PO_4$ - 0.05% | antifoam of approximately |
| $MgSO_4.7H_2O$ - 0.05% | 2000 Dalton molecular |
| P2000+- 0.05% | |
| pH - 5.8 | |

The results of those fermentations are summarized in the following Table 2:

TABLE 2

| | Lovastatin Concentrations | |
|---|---|---|
| Pre-culture Medium | Culture Medium | Lovastatin mg/Liter |
| ME, 20.5 hr | CMP | 26 |
| ME, 20.5 hr | Y5 | 0.6 |
| ME, 20.5 hr | DMP | nil |
| ME, 49 hr | CMP | 26 |
| ME, 49 hr | Y5 | 0.8 |
| ME, 49 hr | DMP | nil |
| 2MY, 20.5 hr | CMP | 19 |
| 2MY, 20.5 hr | Y5 | 0.3 |
| 2MY, 20.5 hr | DMP | 0.2 |
| 2MY, 49 hr | CMP | 22 |
| 2MY, 49 hr | Y5 | 0.9 |
| 2MY, 49 hr | DMP | 0.4 |

Under these conditions, this culture of Coniothyrium sp. in CMP medium produced 19-26 mg/liter of Lovastatin.

Example 2

Coniothyrium fuckelli ATCC 74227 was grown in a sterilizable fermentation apparatus with a volume of 15 Liters. The apparatus was equipped with an agitator, aerator, pH control system, dissolved oxygen control system, and a pump and feed system designed to allow the sterile addition of glucose solutions. The pH was controlled by the automatic addition of ammonium hydroxide or phosphoric acid to maintain the pH of the culture medium constant at 5.0. Periodically, the fermentation broth was sampled, measured for glucose concentration and an addition of glucose was made manually to maintain a concentration of glucose at approximately 2-5 g/Liter. After 192 hours of growth under these conditions, the concentration of biomass reached 65 grams/Liter and the concentration of Lovastatin reached 102 mg/Liter.

Example 3

The result of controlling the glucose concentration at 3–7 g/L was so unusually high in comparison to corresponding shake-flask results that investigations were conducted into the effect of automatically controlling the glucose concentration. This was accomplished by using a specially designed electronic controller to monitor the rate of oxygen consumption by the culture and to pump glucose into the culture when a reduction in the rate of use of oxygen was detected. Periodically, samples were taken from the culture and the glucose concentration was measured. The results of this Example are summarized below in Table 3.

TABLE 3

| glucose | dissolved oxygen | biomass g/L | Lovastatin mg/L |
|---|---|---|---|
| 2.5 g/L | 30–90% | 64 g/L | 146 mg/L |

The results of this experiment show that using an automatic mechanism linked to the rate of oxygen consumption for controlling the concentration of glucose at 3–7 g/L results in luxuriant growth and high concentrations of Lovastatin after only 140 hours of growth.

Example 4

A medium was developed for the growth of *Coniothyrium fuckelii* ATCC 74227, and its composition is as follows:

| | % (w/v) |
|---|---|
| Glucose | 12 |
| Peptone | 2 |
| Amicase | 4 |
| Ammonium Sulfate | 0.8 |
| Magnesium Sulfate | 0.05 |
| P 2000 Antifoam | 0.1 |
| pH | 5.5 |

The fermentation was carried out as before. With this medium, the lovastatin concentration reached 185 mg/L.

Example 5

A further medium for the growth of *Coniothyrium fuckelii* ATCC 74227, has the following composition:

| | % (w/v) |
|---|---|
| Glucose | 12 |
| Peptone | 1 |
| Amicase | — |
| $(NH_4)_2SO_4$ | 0.4 |
| $MgSO_4.7H_2O$ | 0.05 |
| P 2000 | 0.1 |
| pH | 5.5 |
| L - isoleucine | 0.2–1.5 |
| L - aspartic acid | 0.2–1.5 |

With this medium, the lovastatin concentration was 430 mg/Liter.

In all the experiments, the presence of Lovastatin was confirmed by:

HPLC, photiodide array (PDA) detector, TLC, GC/MS and the melting point;

a comparison of the UV Spectra showed LVCOOH peaks and LV peaks corresponding to authentic LVCOOH and LV peaks respectively;

the HPLC had the appropriate retention times for the lactone and acid forms of lovastatin;

the GC/MS of Cs showed corresponding peaks to those of authentic samples; and and the melting point is in the range 170°–171° C.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What I claim is:

1. A process for the preparation of lovastatin which comprises growing *Coniothyrium fuckelii* ATCC 74227 or a lovastatin-producing mutant thereof in a nutrient medium containing assimilable sources of carbon, nitrogen and inorganic salts under aerobic fermentation conditions such that lovastatin is produced and recovering the lovastatin so produced.

2. The process of claim 1 wherein the carbon sources are glucose and corn starch, the nitrogen sources are soybean flour and meat extract and the inorganic salts are sodium chloride, potassium phosphate and magnesium sulfate.

3. The process of claim 1 wherein the carbon source is glucose, the nitrogen source is peptone and the inorganic salts are ammonium sulfate and magnesium sulfate.

4. The process of claim 1 wherein the carbon source is glucose, the nitrogen sources are peptone, L-isoleucine and L-aspartic acid and the inorganic salts are ammonium sulfate and magnesium sulfate.

5. The process of claim 1 wherein the fermentation is carried out as a submerged fermentation.

6. The process of claim 1 wherein the temperature is maintained at about 22° C. to about 30° C.

7. The process of claim 1 wherein the pH is maintained at about 5.0 to about 7.0.

8. The process of claim 1 further comprising the step of germinating spores of the microorganism of the genus Coniothyrium in a pre-culture nutrient medium containing assimilable sources of carbon and nitrogen to produce a vegetative culture of said microorganism.

9. The process of claim 8 wherein the carbon sources present in said pre-culture nutrient medium are glucose and malt extract and the nitrogen source is neopeptone.

10. A biologically pure culture of a microorganism of the strain *Coniothyrium fuckelii* ATCC 74227 or a lovastatin-producing mutant.

* * * * *